United States Patent [19]

Drake et al.

[11] Patent Number: 4,835,330
[45] Date of Patent: May 30, 1989

[54] GLASS POWDER PROMOTER FOR CARBONATE SUPPORTED CATALYST AND OLEFIN DIMERIZATION PROCESSES THEREWITH

[75] Inventors: Charles A. Drake, Nowata; Donald H. Kubicek, Bartlesville, both of Okla.

[73] Assignee: Phillips Petroleum Company, Bartlesville, Okla.

[21] Appl. No.: 185,664

[22] Filed: Apr. 25, 1988

Related U.S. Application Data

[62] Division of Ser. No. 26,249, Mar. 16, 1987, Pat. No. 4,774,215.

[51] Int. Cl.$^4$ .................. B01J 27/232; C07C 2/24
[52] U.S. Cl. ................................ 585/516; 585/530; 502/184
[58] Field of Search ............. 585/510, 511, 516, 530; 502/174, 184

[56] References Cited

U.S. PATENT DOCUMENTS

| | | | |
|---|---|---|---|
| 3,008,943 | 10/1961 | Guyer | 502/60 |
| 3,094,573 | 6/1963 | Hall | 585/516 |
| 3,216,947 | 11/1965 | Wilkes | 585/516 |
| 3,337,473 | 8/1967 | Beroza | 252/442 |
| 3,494,876 | 2/1970 | Bjornson | 252/454 |
| 3,513,106 | 5/1970 | Chapman et al. | 502/202 |
| 4,388,480 | 6/1983 | Imai | 585/516 |
| 4,520,126 | 5/1985 | Kawamoto | 502/184 |
| 4,544,790 | 10/1985 | Drake | 585/516 |
| 4,595,787 | 6/1986 | Drake | 585/516 |
| 4,609,637 | 9/1986 | Drake | 502/174 |

*Primary Examiner*—Patrick P. Garvin
*Assistant Examiner*—George R. Fourson
*Attorney, Agent, or Firm*—Lynda S. Jolly

[57] ABSTRACT

Catalysts and processes for the dimerization or co-dimerization of dimerizable olefins are provided. The catalysts comprise at least one elemental alkali metal and a finely divided glass promoter on an alkali metal carbonate support. Optionally, the support may also contain a carbonaceous component, an inorganic metal oxide or stainless steel. The finely divided glass promoter may be combined with finely divided stainless steel, elemental copper, or elemental cobalt.

18 Claims, No Drawings

GLASS POWDER PROMOTER FOR CARBONATE SUPPORTED CATALYST AND OLEFIN DIMERIZATION PROCESSES THEREWITH

CROSS-REFERENCE TO RELATED APPLICATION

This application is a division of co-pending application Ser. No. 026,249, filed Mar. 16, 1987 now U.S. Pat. No. 4,774,215.

BACKGROUND OF THE INVENTION

This invention relates to alkali metal carbonate supported alkali metal catalysts.

It is known in the art to employ supported alkali metal catalysts for such conversions as propylene dimerization. In addition, the use of alkali metal carbonates as catalyst supports is known in the art. However, such catalysts as alkali metals supported on alkali metal carbonate supports do not always give high yields of the desired products, either due to low feed conversion, low product selectivity, or both. In addition, the use of alkali metal carbonates alone as catalyst supports has been disadvantageous, especially in fixed bed operations, for the reason that the supports do not have sufficient strength. It is also known that the addition of a finely ground metal, such as copper or stainless steel, as a promoter onto the surface of the catalyst support enhances the dimerization activity of the catalyst and provides strength and durability to the catalyst. However, the metal promoters are costly and difficult to process.

SUMMARY OF THE INVENTION

It is an object of this invention to provide an economical and novel promoter for carbonate supported alkali metal catalysts.

It is a further object of this invention to provide a promoter for carbonate supported alkali metal catalysts which lends itself to easy processing.

It is a further object of this invention to provide an improved method for preparing an alkali metal carbonate supported elemental alkali metal catalyst system.

It is yet a further object of this invention to provide an improved catalyst system to enhance the dimerization of olefins.

It is yet a further object of this invention to provide an improved process for the dimerization of olefins.

In accordance with the present invention, finely divided glass is added to a dimerization catalyst system comprising at least one elemental alkali metal on an alkali metal carbonate support. The resulting catalyst system gives good dimerization activity and is rugged and thus useful, for example, in a fixed bed reactor. The finely divided glass is inexpensive and easily processed.

DESCRIPTION OF PREFERRED EMBODIMENTS

The present invention provides a catalyst system which comprises an elemental alkali metal and finely divided glass on an alkali metal carbonate support.

In accordance with another embodiment of the invention, a catalyst system is provided which comprises an elemental alkali metal and finely divided glass supported on an alkali metal carbonate, said support further containing a carbonaceous compound, an inorganic metal oxide, and/or stainless steel.

Supports

Commercially available alkali metal carbonate in the form of a powder, pellets, granules or the like can be treated directly with at least one alkali metal and one or more of the desired promoting metals as discussed more fully below. This form of support has the advantage of being most readily obtained with a minimum of handling. In some circumstances, a large particle size and/or more rugged form of catalyst support is desired, such as, for example, where fixed bed reactions, especially large volume fixed bed reactions, are carried out.

In accordance with a particular technique for the support preparation, commercially available alkali metal carbonate is mixed with just enough water to form a thick paste. The thick paste is then oven dried under conditions of time and temperature sufficient to insure that substantially all water has been driven off. The dried paste is then broken up into pieces and fractionated by suitable means such as for example by passing through appropriate mesh size screen sieves to recover a desired particle size fraction. Although one skilled in the art of catalyst preparation can readily determine what ratios of alkali metal carbonate to water are suitable for the preparation of a thick paste, in order to provide guidance, it is suggested that an alkali metal carbonate: water weight ratio of at least about 3.5:1 be employed. The resulting catalyst support particles will be referred to hereinafter as "wet process" potassium carbonate support.

In accordance with another technique for the support preparation commercially available alkali metal carbonate is (1) mixed with a non-acidic inorganic oxide and/or finely divided stainless steel in a weight ratio of about 1:1 to about 1:10 alkali metal carbonate: inorganic oxide and/or finely divided stainless steel, (2) heated to at least about 950° C., (3) then cooled to about 80°–100° C. for treatment with one or more components as discussed more fully below. Catalyst support prepared in this manner will be referred to hereinafter as "melt process" alkali metal carbonate support.

The term "non-acidic inorganic oxide support" is intended to include those inorganic oxide materials which have low double bond isomerization activity under the reaction conditions employed for olefin dimerizaton. Suitable materials include but are not limited to alumina, silica, silica-alumina, magnesia-titania, thoria, magnesia, titania, zirconia and the like and mixtures of any two or more thereof. Alumina and silica-alumina are preferred because of their ready availability, ease of handling and resultant good catalyst activity.

In accordance with yet another technique for the support preparation an alkali metal carbonate catalyst support with greatly improved physical integrity results when finely divided stainless steel in amounts of up to about 80 weight percent based on total catalyst weight is blended with alkali metal carbonate prior to or simultaneous with the treatment of the support with one or more metals and finely divided glass as discussed more fully below. Catalyst support prepared in this manner will be referred to hereinafter as "metal containing" alkali metal carbonate support.

The term "stainless steel" as used herein is intended to cover broadly those alloys of iron which are relatively inert to the reaction conditions employed for the dimerization of olefins. Contemplated materials include, but are not limited to type 303 stainless steel, type 316 stainless steel, type 410 stainless steel, type 431 stainless steel, Hastelloy C, and the like. Type 316 stainless steel is presently preferred because of its relatively low cost, ready availability, and resultant good catalyst activity.

In accordance with another technique for the support preparation, an alkali metal carbonate catalyst support is prepared by first pelletizing a mixture of alkali metal carbonate and about 0.1–10 weight percent of at least one carbonaceous compound. For purposes of this disclosure, the term "carbonaceous compound" is intended to include various forms of the element carbon, including, but not limited to carbon black, charcoal, coconut charcoal, amorphous graphite, crystallite graphite, and the like, as well as mixtures of any two or more thereof. Finely divided graphite is presently preferred because it is useful both as a die lubricant for the pelleting process and it imparts dramatically improved activity to the finished dimerization catalyst.

The actual pelleting operation of the alkali metal support containing a carbonaceous compound can be carried out in any suitable pelleting apparatus. If desired, lubricants such as stearic acid, rosin, hydrogenated coconut oil, and the like can also be added to the potassium carbonate-carbonaceous compound mixture to be pelleted.

The pelleted support can then be subjected directly to the next step, i.e., partial oxidation, or can optionally be ground into smaller size particles if desired for subsequent use.

The pelleted support, either as the pellets or as smaller crushed particles, is then heated in an oxygen-containing atmosphere under conditions suitable to oxidize in the range of about 10–90% of the carbonaceous compound. Suitable oxidation conditions are temperatures in the range of about 200°–900° C. for a time in the range of about 0.1 to 48 hours are generally suitable. Longer contact times will generally be appropriate at lower treatment temperatures and conversely, shorter contact times will be appropriate at higher treatment temperatues. Presently preferred treatment temperatures are in the range of about 250°–600° C. for a treatment time of about 0.5 to 6 hours. Such treatment conditions will be expected to cause oxidation of at least 20% of the carbonaceous compound, but less than about 80% of the carbonaceous compound. Most preferably, treatment conditions which cause the oxidation of about 30 to 70% of the carbonaceous compound will be employed. As a result of this partial oxidation of the pelleted support, the concentration of carbonaceous compound remaining on the surface of the support is substantially less than the concentration of carbonaceous compound remaining in the interior portions of the support. Catalyst support prepared in this manner will be referred to hereinafter as "carbon containing" alkali metal carbonate support.

The pelleted, oxidized "carbon containing" alkali metal carbonate support can then be subjected directly to the next step, i.e., treatment with at least one catalytically active material, or can optionally be ground into smaller size particles if desired for subsequent use.

It is of course recognized by those of skill in the art that pellets of most any desired size can be prepared, e.g., ⅛ inch, 3/16 inch, ¼ inch, ⅜ inch, etc.

Catalysts and Promoters

Catalysts supports employed in the practice of this invention comprise one of the alkali metal carbonate supports described above, at least one elemental alkali metal catalyst, finely divided glass as a promoter and optionally one or more of the following additional metallic promoters:
elemental copper,
elemental cobalt,
finely divided stainless steel, and
mixtures of two or more thereof.

It should be recognized, however, that the catalysts systems of the invention can contain additional components which do not adversely affect the catalyst performance, such as, for example, pigments, dyes, processing aids, inert fillers, binders and the like.

The alkali metals contemplated to be within the scope of the invention include lithium, sodium, potassium, rubidium and cesium. While the proportion of alkali metal combined with the alkali metal carbonate support can vary appreciably, generally at least about one weight percent of alkali metal based on the total weight of treated support will be employed. Generally, about 1 to about 20 weight percent alkali metal will b employed with about 2 to about 15 weight percent preferred. An alkali metal loading of about 3 to about 10 weight percent based on the total weight of treated support is most preferred for most efficient use of reagents, high catalyst activity and selectivity, and ease of catalyst preparation. Potassium is the preferred elemental alkali metal due to its ready availability as well as ease and safety in handling.

The term "glass" as used herein is intended to cover broadly those compounds composed primarly of silicon oxides. Specifically, the silica content of the glass should be 8 percent or greater. Contemplated materials include, but are not limited to, "vycor" glass, "crown" glasses, "flint" glasses, pyrex type borosilicate glasses, kimax type borosilicate glasses, borosilicate crown glasses, barium crown glasses, soda-lime glasses, potassium glass and iron glass. The glass must also have a low surface area, less than about 2 square meters per gram ($m^2$/gm) of glass, preferably 1 $m^2$/gm or less, a melting point above 250° C., and not exhibit any olefin dimerization activity at reaction conditions. The particle size of the finely divided glass can vary, but generally, at least 1 to about 1000 microns will be employed, with about 5 to about 200 microns preferred. This type of essentially non-porous finely divided glass is frequently referred to in the art as having no surface area. Borosilicate crown glass is presently preferred because of its relatively low cost, ready availability and resultant good catalyst activity. Other suitable materials include commercially available low surface area silica compositions known in the art as catalyst carriers (less than 2 $m^2$/gm surface area), such as, for example that sold by Norton Chemical Process Company under the designation SS5131.

The proportion of the finely divided glass promoter combined with the alkali metal carbonate support can vary appreciably, but generally, at least 1 to about 50 weight percent of the finely divided glass based on the total weight of treated carbonate support will be employed, with about 3 to about 25 weight percent preferred, and about 2 to about 15 weight percent presently more preferred.

The proportion of optional metallic promoter combined with finely divided glass and supported on the potassium carbonate support cam vary appreciably, but generally, at least one weight percent of the optional metallic promoter based on the total weight of treated support will be employed. The following amounts are provided for additional guidance:

| | Loading, Weight Percent | | |
|---------|-------|--------------|-----------|
| Promoter | Broad | Intermediate | Preferred |
| Cu | 1–30 | 3–20 | 5–12 |
| Co | 1–50 | 3–25 | 5–15 |
| *SS | 1–80 | 3–60 | 5–50 |

*SS = Stainless Steel

The general procedure for preparation of the catalyst systems of the invention involves heating the alkali metal carbonate support, following the optional oxidation step, to a temperature in the range of about 80° to about 350° C., preferably to about 250° C. in an oxygen-free atmosphere, such as, for example $N_2$, Ar or the like, cooling the pelletized support and then contacting the pelletized support with at least one elemental alkali metal at a temperature sufficient to cause the alkali metal to melt. The contacting, done in an oxygen-free atmosphere, is preferably carried out with vigorous stirring to ensure even distribution. Suitable temperatures for the contacting step will vary with the particular alkali metal employed. For example, with elemental potassium, temperatures in the range of about 80° to 100° C. are preferred, while with elemental sodium, temperatures in the range of about 100° to 140° C. are preferred.

While the alkali metal treated support is maintained at or above about 80° C., in an oxygen-free atmosphere, finely divided glass and any other desired metallic promoter(s), such as for example, elemental copper, can be gradually added while the treated catalyst is continuously stirred. Generally, temperatures in the range of about 80° to about 100° C. are employed. The catalyst system is then ready to be charged to the reactor.

Optionally, the alkali metal carbonate support, once elemental alkali metal, finely divided glass and any additional desired promoters have been desposited thereon, can be subjected to a subsequent heating step to ensure as uniform a distribution as possible of the various promoting metals on the surface of the alkali metal carbonate support. Thus, the finished catalyst can be subjected to a temperature in the range of at least about 150° C. for a time in the range of about 0.1 to 4 hours. A temperature in the range of about 250°–350° C. for a time in the range of about 0.5–2 hours is presently preferred for the most uniform distribution.

Optionally, prior to charging the reactor, the catalyst system can be mixed with an inert substance to dilute the catalyst system and decrease the rate of olefin dimerization. Any inert substance which has no catalytic activity in an olefin dimerization reaction can be used. One example of such an inert substance in glass beads.

As indicated by the variety of supports, alkali metal components, finely divided glass and metallic promoters included within the scope of the invention, numerous catalyst combinations are possible. Any combination of the alkali metal, finely divided glass and optional metallic promoters disclosed can be supported on any alkali metal carbonate support disclosed. Thus, for example, wet process potassium carbonate support can be treated with elemental potassium, finely divided glass, elemental copper and elemental cobalt to provide an active and selective catalyst. Similarly, carbon containing potassium carbonate support can be treated with elemental alkali metal such as for example, potassium, and finely divided glass only; or the same support can be treated with elemental potassium plus finely divided glass plus stainless steel plus elemental copper and so on. The most preferred embodiment of the invention is a combination wherein elemental potassium and finely divided glass are supported on a carbon containing potassium carbonate support. Some possible combinations are described in detail in the examples which follow. The combination of support, alkali metal and promoter(s) which one may choose to employ will depend on a variety of variables such as for example, reactor configuration, reaction temperature and pressure, olefin feed employed, rate of olefin feed, and conversions desired.

Reactants

Reactants applicable for use in the process of the invention are olefinic compounds which can (a) self-react, i.e., dimerize, to give useful products such as, for example, the self-reaction of propylene gives 4-methyl-1-pentene; and/or (b) olefinic compounds which can react with other olefinic compounds, i.e., co-dimerize, to give useful products such as, for example, co-dimerization of ethylene plus propylene gives 1-pentene, co-dimerization of ethylene and 1-butene gives 3-methyl-1-pentene and so forth. As used herein, the term "dimerization" is intended to include both self-reaction and "co-dimerization" as defined above.

Suitable dimerizable olefinic compounds are those compounds having from about 3 to about 30 carbon atoms and having at least one olefinic double bond and at least one allylic hydrogen atom, i.e., at least one hydrogen atom attached to a carbon atom adjacent to a double-bonded carbon atom. Exemplary compounds include, but are not limited to, acyclic and cyclic olefins such as for example propylene, 1-butene, 2-butene, isobutylene, 1-pentene, 2-pentene, 1-hexene, 2-hexene, 3-hexene, 1-heptene, 2-heptene, 3-heptene, the four normal octenes, the four normal nonenes and so forth; 3-methyl-1-butene, 2-methyl-2-butene, 3-methyl-1-pentene, 3-methyl-2-pentene, 4-methyl-1-pentene, 4-methyl-2-pentene, tetramethylethylene and the like; cyclopentene, cyclohexene, methylcyclopentene, methylcyclohexene, and the like and mixtures of any two or more thereof.

Suitable co-dimerizable olefinic compounds are those compounds having from about 2 to about 30 carbon atoms, including all the compounds contemplated within the scope of "dimerizable" olefinic compounds as indicated above. In addition, olefinic compounds which do not have at least one allylic hydrogen atom are also included within the scope of co-dimerizable olefins. Exemplary compounds in addition to those indicated above, include, but are not limited to ethylene, 3,3-dimethyl-1-butene, ditertiarybutyl ethylene and the like and mixtures of any two or more thereof.

The compounds indicated above as dimerizable olefinic compounds are capable of undergoing both self-reaction, i.e., dimerization, and cross-reaction, i.e., co-dimerization, with other members of the same group or with those compounds designated as co-dimerizable. The co-dimerizable compounds which do not have at least one allylic hydrogen may be capable of isomerization to form an olefin having an allylic hydrogen under the reaction conditions employed. If such isomerization is not possible, then those non-isomerizable, co-dimerizable compounds which do not have at least one allylic hydrogen must be contacted with at least one of the "dimerizable" compounds in order to facilitate the desired co-dimerization reaction. In other words, the co-dimerizable compounds which do not have at least one allylic hydrogen atom and are not capable of isomerization to produce an olefin having at least one allylic hydrogen are therefore not capable of reacting with themselves under the reaction conditions employed for the dimerization reaction.

Reaction Conditions

The dimerization reaction of the invention can be carried out using either batch or continuous type of operation, although the catalysts of the invention are particularly well suited for continuous, fixed bed, operation. Suitable equipment such as for example autoclaves, tubular reactors and the like as are well known in the art can be employed. No special materials of construction are required so that steel, stainless steel, glass-lined reactors, or the like can be employed.

The reaction temperature can vary depending on the catalyst and feed(s) employed. Typically, a temperature range of about 50° to about 250° C. is suitable. Temperatures of about 80° to about 200° C. are preferred with a range of about 120° to about 160° C. most preferred because optimum reaction rates are obtained with minimum by-product formation.

The dimerization reaction can be carried out by contacting the dimerizable olefins with catalyst in the liquid phase or the gas phase, depending on the structure and molecular weight of the olefin, as well as reaction temperature and pressure employed. Pressure during the dimerization reaction can vary between wide limits. In general, higher pressures favor the progress of the reaction. Thus, pressures of atmospheric up to about 10,000 psig and higher are suitable. Preferably, pressures of about 100 to about 5,000 psig are employed, with pressure of about 1,000 to about 4,000 psig most preferred in order to achieve a good balance between reaction rate and minimize equipment and operating costs necessitated by very high reaction pressures.

If the reaction is carried out in the liquid phase, solvents or diluents for the reactants can be used. Saturated aliphatic hydrocarbons, e.g., pentane, hexane, cyclohexane, dodecane; aromatic compounds, preferably those without an alpha-hydrogen (which would be capable of undergoing alkylation under the reaction conditions) such as benzene and chlorobenzene are suitable. If the reaction is carried out in the gaseous phae, diluents such as aliphatic hydrocarbons, for example methane, ethane and/or substantially inert gases, e.g., nitrogen, argon, can be present.

The contact time required for the dimerization reaction depends upon several factors such as for example the activity of the catalyst, temperature, pressure, structure of the reactants employed, level of conversion desired, and the like. The length of time during which the dimerizable olefinic compounds are contacted with catalyst can vary conveniently between about 0.1 seconds and about 24 hours although shorter and longer contact times can be employed. Preferably, times of about one minute to about 5 hours are employed. Where reaction is carried out in continuous fashion, it is convenient to express the reactant/catalyst contact time in terms of weight hourly space velocity (WHSV), i.e., the ratio of the weight of reactant which comes in contact with a given weight of catalyst per unit time. Thus, a WHSV of about 0.1 to about 10 will be employed. A WHSV of about 0.5 to about 5 is preferred, with about 1 to about 4 WHSV most preferred for optimum catalyst productivity.

Products

The olefinic products of the invention have established utility in a wide variety of applications such as for example as monomers for use in the preparation of homopolymers, copolymers, terpolymers, e.g., as the third component of the ethylene-propylene terpolymers useful as synthetic elastomers, and the like.

A further understanding of the present invention and its advantages will be provided by reference to the following examples.

EXAMPLE 1

Catalyst Preparation

Catalyst support was prepared by pelleting commercially available anhydrous potassium carbonate on a Stokes-Pennwalt Model 900-511-6 Eureak Tabletting Machine. Pellets (⅛") were prepared and used directly, or crushed and sieved to recover a desirable particle size. The potassium carbonate was admixed with one weight percent of graphite prior to subjecting to the pelleting process.

After pelleting, the potassium carbonate pellets (or crushed, sieved material) were subject to a "burnoff" (oxidation) period in an oxygen-containing atmosphere at a temperature of about 350° C. for a period of about 3 hours.

Following burnoff treatment, the support was allowed to cool, in an oxygen-free atmosphere, to about 80° to about 85° C., at which time, about 5 weight percent of elemental potassium, and optionally, about 5 weight percent of finely divided glass, and optionally, about 5 weight percent of finely divided stainless steel were added. Specifically, the finely divided glass used in one practice of this invention was Owens Corning Fiberglass milled fibers-powder; the fibers were smaller than 50 microns and had a surface area of less than 2 $m^2/gm$. The glass was a borosilicate crown glass composition. The elemental potassium and optional promoter were thoroughly contacted with the catalyst support.

EXAMPLE 2

Dimerization of Propylene

Typically, the dimerization of propylene was carried out in a steam heated 316 stainless steel tubular reactor (½"×20"). The catalyst system (27 grams; density 0.84 g/mL), bonded above and below by small volumes of glass beads, was combined with 25 grams of an inert substance, i.e., no dimerizition catalytic activity, to dilute the catalyst system and thus reduce and control the reaction rate. The contents of the tubular reactor were heated to the reaction temperature of about 160° C. at about 1500 psig and propylene was pumped into the reactor at a rate of about 120 mL/hr. After about 1.5 hours of reaction time and each one hour thereafter for the following 6 hours except for Control B, where only 5 samples were collected and analyzed, a sample was collected and analyzed by gas liquid chromatography (glc). Results of numerous propylene dimerization reactions are summarized in Table I.

TABLE I

| Run No. | Catalyst | Promoter(s) | Propylene Conv., % | Selectivity to 4MP1, % | 4MP1/4MP2 |
|---|---|---|---|---|---|
| 1 | Control A | K | 1.9 | 88 | 22 |
| 2 | Control A | K | 4.6 | 88 | 22 |
| 3 | Control A | K | 6.8 | 89 | 24 |
| 4 | Control A | K | 7.4 | 89 | 29 |
| 5 | Control A | K | 8.7 | 90 | 32 |
| 6 | Control A | K | 8.3 | 90 | 33 |
| 7 | Control B | K, SS* | 6.1 | 88 | 22 |
| 8 | Control B | K, SS | 10.9 | 89 | 28 |
| 9 | Control B | K, SS | 12.3 | 90 | 31 |
| 10 | Control B | K, SS | 13.6 | 90 | 32 |
| 11 | Control B | K, SS | 18.5 | 90 | 33 |
| 12 | Invention C | K, glass | 7.6 | 89 | 31 |
| 13 | Invention C | K, glass | 11.5 | 89 | 31 |
| 14 | Invention C | K, glass | 15.5 | 89 | 29 |
| 15 | Invention C | K, glass | 18.0 | 89 | 27 |
| 16 | Invention C | K, glass | 18.5 | 89 | 29 |
| 17 | Invention C | K, glass | 19.4 | 89 | 29 |

*SS = Stainless Steel

Invention catalyst C yielded improved propylene conversion to 4-methyl-1-pentene relative to control catalyst A and control catalyst B. In addition, invention catalyst C produced an equivalent or slightly higher 4-methyl-1-pentene (4MP1) to 4-methyl-2-pentene (4MP2) ratio than the control catalysts. Since the separation of 4MP1 and 4MP2 is quite difficult, high ratios of 4MP1 to 4MP2 are desirable for recovery of high purity 4MP1.

The catalysts were visually inspected after about 7.5 hours of dimerization reaction time. Control catalyst A was mostly fine particles and the support had almost all collapsed. Control catalyst B and some fines and some support damage. Invention catalyst C showed some fines and a small amount of support damage. Durability of the catalyst support and the prevention of the production of fine particles in the reactor bed is necessary to prevent reactor plugging.

The examples have been provided merely to illustrate the practice of the invention and should not be read so as to limit the scope of the invention or the appended claims in any way. Reasonable variations and modifications, not departing from the essence and spirit of the invention, are contemplated to be within the scope of patent protection desired and sought.

What is claimed is:

1. A process for the dimerization of at least one dimerizable olefin which comprises contacting said olefin under dimerization conditions with a catalyst system comprising:
   (a) at least about 1 wt.% of at least one an elemental alkali metal,
   (b) at least about 1 wt% of finely divided glass, and
   (c) an alkali metal carbonate support; wherein components (a) and (b) are supported on component (c).

2. A process according to claim 1 wherein said contacting is carried out at a temperature in the range of about 50° to about 250° C., a pressure in the range of about 100 to about 10,000 psig, and a weight hourly space velocity in the range of about 0.1 to about 10.

3. A process according to claim 1 wherein said finely divided glass comprises non-porous silicon dioxide with a surface area of less than 2 m²/gm.

4. A process according to claim 1 wherein said finely divided glass has a particle size within the range of about 1 to about 1000 microns.

5. A process according to claim 4 wherein said finely divided glass has a particle size within the range of about 5 to about 200 microns.

6. A process according to claim 1 wherein said finely divided glass is present in an amount within the range of about 1 to about 50 weight percent of the alkali metal carbonate support.

7. A process according to claim 6 wherein said finely divided glass is present in an amount within the range of about 2 to about 15 weight percent of the alkali metal carbonate support.

8. A process according to claim 1 wherein said elemental alkali metal is potassium.

9. A process according to claim 1 wherein said dimerizable olefin is selected from the group consisting of propylene, ethylene, and mixtures thereof.

10. A process according to claim 1 wherein said potassium carbonate support further comprises a carbonaceous compound, wherein said carbonaceous compound is selected from the group consisting of carbon black, charcoal, coconut charcoal, amorphous graphite, crysallite graphite and mixtures thereof.

11. A process according to claim 1 wherein said alkali metal carbonate supply further comprises an inorganic oxide.

12. A process according to claim 11 wherein said inorganic oxide comprises alpha alumina.

13. A process according to claim 1 wherein said catalyst system further comprises a promoter selected from the group consisting of finely divided stainless steel, elemental copper, elemental cobalt, and mixtures thereof.

14. A process for the production of 4-methyl-1-pentene which comprises contacting propylene under dimerization conditions with a catalyst system comprising:
   (a) elemental potassium
   (b) finely divided glass, and
   (c) a potassium carbonate support; wherein components (a) and (b) are supported on component (c).

15. A process according to claim 14 wherein said contacting is carried out at a temperature in the range of about 80° to about 200° C., a pressure in the range of about 1000 to about 4000 psig, and a weight hourly space velocity in the range of about 0.1 to about 10.

16. A process according to claim 15 wherein said finely divided glass comprises a borosilicate crown glass with a surface area of less than 2 m²/gm.

17. A process for preparing a catalyst system which comprises:
   (a) heating an alkali metal carbonate containing mixture,
   (b) cooling said alkali metal carbonate containing mixture,
   (c) contacting said alkali metal carbonate containing mixture with an elemental alkali metal by stirring, and
   (d) contacting said alkali metal carbonate containing mixture and said elemental alkali metal with finely divided glass.

18. A process according to claim 17 wherein:
   (a) said alkali metal carbonate containing mixture is made by mixing potassium carbonate and amorphous graphite;
   (b) the thus mixed potassium carbonate and amorphous grahite is heated to a temperature in the range of about 200° to about 900° C., in an oxygen ambient, for a time in the range of about 0.1 to about 48 hours to partially oxidize said graphite;
   (c) the thus treated composition of (b) is then cooled in an oxygen-free ambient to a temperature in the range of about 80° to about 350° C.; and
   (d) wherein said elemental potassium and said finely divided glass are simultaneously contacted with said potassium carbonate by said stirring.

* * * * *